United States Patent [19]

Brayer et al.

[11] Patent Number: 5,194,622

[45] Date of Patent: Mar. 16, 1993

[54] PROCESS FOR PREPARATION OF THIAZOLYLALKOXY ACRYLATES

[75] Inventors: Jean-Louis Brayer, Nanteuil le Haudoin; Jean-Pierre Demoute, Neuilly Plaisance, both of France

[73] Assignee: Roussel Uclaf, Paris, France

[21] Appl. No.: 793,862

[22] Filed: Nov. 18, 1991

[30] Foreign Application Priority Data

Nov. 21, 1990 [FR] France .................. 90 14496

[51] Int. Cl.⁵ .......................................... C07D 277/20
[52] U.S. Cl. ...................................... 548/204; 548/236;
548/341.1; 548/248; 548/311.4; 548/311.1;
548/315.4; 548/315.7; 548/316.7; 548/317.1;
548/323.5; 548/325.1; 548/342.1; 560/55;
544/133; 544/137; 544/139; 544/238; 544/369;
544/370; 546/275; 546/276; 546/280
[58] Field of Search ..................... 568/9, 11; 548/204,
548/236, 341; 560/55

[56] References Cited

U.S. PATENT DOCUMENTS

| | | | |
|---|---|---|---|
| 2,946,824 | 7/1960 | Chiddix | 568/9 |
| 3,524,886 | 8/1970 | Fried | 568/9 |
| 4,927,960 | 5/1990 | Maeda | 568/9 |
| 4,937,372 | 6/1990 | Wenderoth et al. | 560/55 |
| 5,003,101 | 6/1990 | Brand et al. | 560/55 |
| 5,041,618 | 8/1991 | Brand et al. | 560/55 |

FOREIGN PATENT DOCUMENTS 0402246 12/1990 European Pat. Off. ............ 548/204

OTHER PUBLICATIONS

Schuetz et al. Chem. Abstr. vol. 113 entry 152422h (1990).

*Primary Examiner*—Donald G. Daus
*Attorney, Agent, or Firm*—Bierman and Muserlian

[57] ABSTRACT

A process for the preparation of a compound of the formula

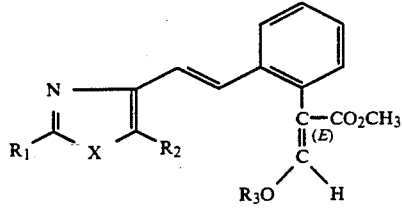

I wherein $R_1$ and $R_2$ are individually selected from the group consisting of hydrogen, halogen, —$CF_3$, alkyl, alkoxy and alkylthio of 1 to 8 carbon atoms, alkenyl and alkynyl of 2 to 8 carbon atoms, —$SO_2$alk and alk is alkyl of 1 to 8 carbon atoms, optionally substituted aryl, aryloxy and arylthio of 6 to 18 carbon atoms and optionally substituted heteroaryl, heteroaryloxy and heterocyclic of 5 to 6 ring members, $R_3$ is selected from the group consisting of alkyl of 1 to 8 carbon atoms, alkenyl and alkynyl of 2 to 8 carbon atoms, aryl of 6 to 18 carbon atoms and alkoxyalkoxyalkyl of 3 to 14 carbon atoms, X is selected from the group consisting of —O—, —S— and —$NR_4$—, $R_4$ is selected from the group consisting of hydrogen, alkyl, alkenyl and alkynyl of up to 8 carbon atoms, —$SO_2$ alkyl, —$SO_2$ alkenyl and —$SO_2$ alkynyl of up to 8 carbon atoms and optionally substituted aryl and —$SO_2$ aryl of 6 to 18 carbon atoms, the double bond between the heterocycle of 5 member ring and the aromatic nucleus is of E and/or Z geometry comprising reacting a halide of the formula

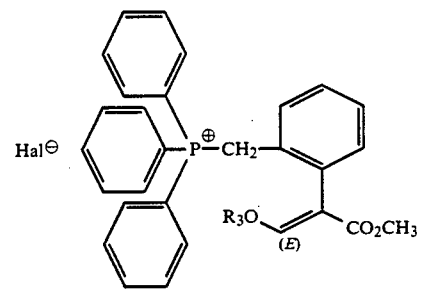

II wherein $R_3$ is as defined above and Hal is hydrogen with a compound of the formula

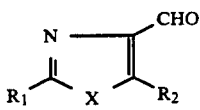

III wherein X, $R_1$ and $R_2$ have the above definitions in the presence of a base to obtain the corresponding product of formula I in the form of a mixture of isomers and optionally separating the isomers and novel intermediates of formula II.

6 Claims, No Drawings

PROCESS FOR PREPARATION OF THIAZOLYLALKOXY ACRYLATES

STATE OF THE ART

U.S. patent application Ser. No. 533,505 filed June 5, 1990 now abandoned in favor of continuation application Ser. No. 788,875 pending filed Nov. 7, 1991 describes a process for the preparation of compounds of formula I comprising reacting a compound of the formula:

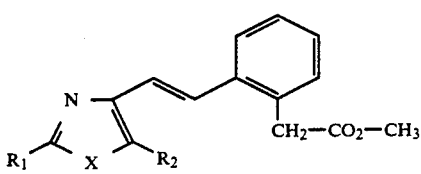

wherein X, $R_1$ and $R_2$ have the above definition with a strong base and an alkyl formate or N-formate or N-formylimidazole to obtain a compound of the formula:

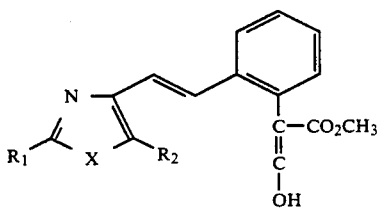

which is reacted with an agent capable of introducing $R_3$, then optionally the different isomers are separated and a process wherein a compound of the formula:

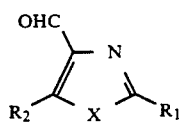

wherein X, $R_1$ and $R_2$ have the above definitions is subjected to the Wittig-Horner reaction with a compound of the formula:

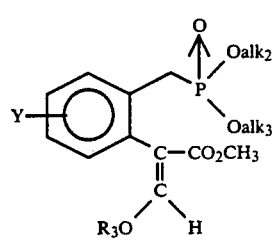

wherein Y and $R_3$ have the above definitions and $alk_2$ and $alk_3$ are individually alkyl of 1 to 8 carbon atoms and optionally the different isomers are separated.

OBJECTS OF THE INVENTION

It is an object of the invention to provide an improved process for the preparation of the compounds of formula I and novel intermediates.

This and other objects and advantages of the invention will become obvious from the following detailed description.

THE INVENTION

The novel process of the invention for the preparation of a compound of the formula

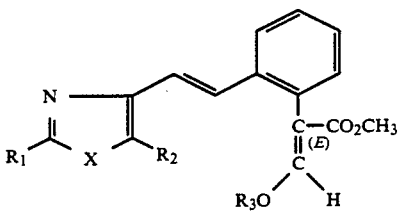

wherein $R_1$ and $R_2$ are individually selected from the group consisting of hydrogen, halogen, —$CF_3$, alkyl, alkoxy and alkylthio of 1 to 8 carbon atoms, alkenyl and alkynyl of 2 to 8 carbon atoms, —$SO_2$alk and alk is alkyl of 1 to 8 carbon atoms, optionally substituted aryl, aryloxy and arylthio of 6 to 18 carbon atoms and optionally substituted heteroaryl, heteroaryloxy and heterocyclic of 5 to 6 ring members, $R_3$ is selected from the group consisting of alkyl of 1 to 8 carbon atoms, alkenyl and alkynyl of 2 to 8 carbon atoms, aryl of 6 to 18 carbon atoms and alkoxyalkoxyalkyl of 3 to 14 carbon atoms, X is selected from the group consisting of —O—, —S— and —$NR_4$—, $R_4$ is selected from the group consisting of hydrogen, alkyl, alkenyl and alkynyl of up to 8 carbon atoms, —$SO_2$ alkyl, —$SO_2$ alkenyl and —$SO_2$ alkynyl of up to 8 carbon atoms and optionally substituted aryl and —$SO_2$ aryl of 6 to 18 carbon atoms, the double bond between the heterocycle of 5 member ring and the aromatic nucleus of E and/or Z geometry comprises reacting a halide of the formula

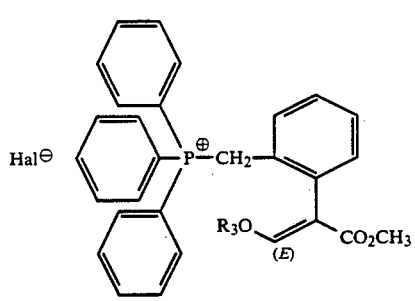

wherein $R_3$ is as defined above and Hal is halogen with a compound of the formula

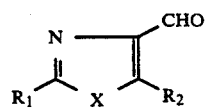

wherein X, $R_1$ and $R_2$ have the above definitions in the presence of a base to obtain the corresponding product of formula I in the form of a mixture of isomers and optionally separating the isomers.

In the addition of the various substituents, alkyl and alkoxy preferably are methyl, ethyl, n-propyl, isopropyl, n-butyl, isobutyl, sec-butyl or tert-butyl, methoxy, ethoxy, isopropoxy, propoxy, butoxy and tert-butoxy;

alkenyl preferably is vinyl, allyl or 1,1-dimethylallyl; alkynyl preferably is ethynyl or propynyl; aryl preferably is phenyl and aryloxy is phenoxy; heteroaryl preferably is furyl, pyridinyl, piperazinyl, benzofuranyl, isobenzofuranyl, oxazolyl, isoxazolyl, phenylthio or thiazolyl; heterocyclic preferably is morpholinyl, pyranyl or pyridazinyl; alkoxyalkoxyalkyl preferably is methoxyethoxyalkyl or has the formula:

$(CH_2)_p$—O—$(CH_2)_{p'}$—O—alkyl wherein p and p' are individually the numbers 1, 2, 3 and 4 and "alkyl" is alkyl of 1 to 8 carbon atoms; and halogen preferably is fluorine or chlorine.

For alkoxyalkyl, thioalkoxy, SO$_2$-alkyl, SO$_2$alkenyl, SO$_2$-alkynyl, aryloxy, heteroaryloxy, SO$_2$-aryl, the alkyl, alkenyl, alkynyl, aryl, aryloxy, and heteroaryl are preferably the above-mentioned radicals.

When aryl, aryloxy, thioaryl, heterocyclic, heteroaryl or heteroaryloxy are substituted, the substituents are preferably selected from the group consisting of free, esterified or etherified hydroxyl in which the ester or ether part contains 1 to 18 carbon atoms such as acetoxy or methoxy, ketone and oxime functions, the saturated or unsaturated, linear, branched or cyclized alkyls contain 1 to 18 carbon atoms such as methyl, ethyl, propyl, isopropyl, ethenyl or ethynyl, halogen such as fluorine, chlorine and bromine, —CF$_3$, —SCF$_3$, —OCF$_3$, —NO$_2$, —NH$_2$ or C≡N.

In a preferred mode of the process, the base present for the reaction of the compounds of formulae II and III is sodium hydride, alkali metal or alkaline earth metal alcoholate, an alkali metal amide or a secondary or tertiary amine in the presence of lithium bromide. The halogen is preferably bromine and the base most preferably is sodium hydride or a secondary or tertiary amine in the presence of lithium bromide.

The Z isomer configuration inversion of the compounds of formula I with a double bond between the aromatic ring and the heterocycle of 5 ring members is preferably effected with iodine as shown in the examples.

The compounds of formula I are described in U.S. patent application Ser. No. 788,875 and the process of the invention has the advantage of very good yields of the compounds of formula I. The compounds have a good fungicidal activity.

The compounds of formula II can be prepared by the following reaction diagram:

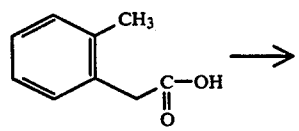

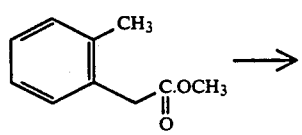

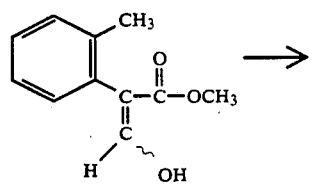

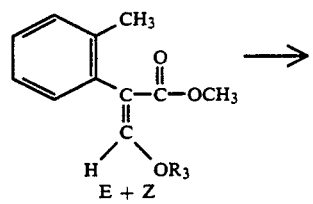

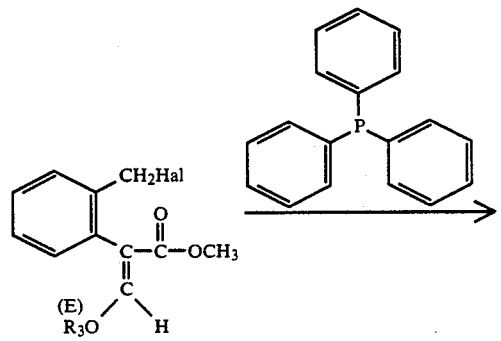

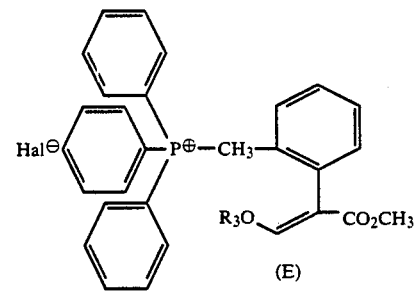

The products of formula II are new industrial products and preferred is [[2-[1-(methoxycarbonyl)-2-methoxyethenyl]-phenyl]-methyl]-triphenyl phosphonium bromide.

The compounds of formula III can be prepared as described in U.S. patent application No. 788,875 by the following reaction diagram:

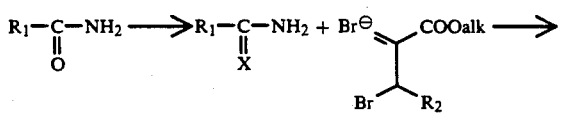

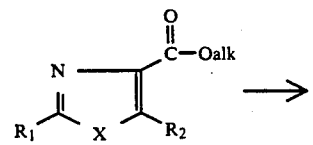

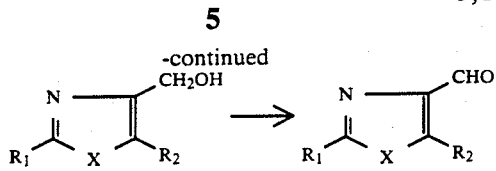

in which $R_1$, $R_2$ and X are defined as above.

In the following examples, there are described several preferred embodiments to illustrate the invention. However, it is to be understood that the invention is not intended to be limited to the specific embodiments.

EXAMPLE 1

Methyl (E,E) α-(methoxymethylene)-2-[2-(4-thiazolyl)-ethenyl]-benzene-acetate.

Operating method 1

7 ml of diisopropylamine were added at −20° C. to a mixture of 10.8 g of lithium bromide in 75 ml of tetrahydrofuran and the mixture was stirred for 10 minutes at −10° C., then poured at 0° C. into a mixture of 27.5 g of [[2-[1-(methoxycarbonyl)-2-methoxyethenyl]-phenyl]-methyl]-triphenyl phosphonium bromide [obtained as in preparation 1], 500 ml of tetrahydrofuran and 5 g of 4-thiazolyl methanal [U.S. patent application No. 788,875]. The reaction medium was stirred for 2 hours at 0° C., then for 48 hours at 20°–25° C. The reaction medium was poured into water, followed by stirring and extraction with methylene chloride. The organic phases were dried and evaporated to dryness and the 15 g of crude product obtained were chromatographed on silica to obtain 7.5 g of the desired E,E isomer melting at 117° C. and 2.8 g of the Z,E isomer.

| NMR Constants | $\delta H_1$ | $\delta H_2$ | $JH_1H_2$ | $\delta H_3$ |
|---|---|---|---|---|
| E,E | 7.10 | 7.42 | 16 | 7.64 |
| Z,E | 6.62 | 6.75 | 12 | 7.49 |

Operating method 2

0.48 g of sodium hydride (50% in oil) were introduced between −5° and −10° C. into a solution of 5.5 g of phosphonium bromide (preparation 1) and 1.1 g of 4-thiazolyl methanal in 50 ml of tetrahydrofuran and 50 ml of dimethylformamide and the reaction medium was maintained at 0° C. for 30 minutes. The mixture was poured into water, followed by stirring and extracting with methylene chloride. The organic phases were dried and evaporated to dryness to obtain 5 g of a crude oil which was chromatographed on silica as previously to obtain 1.25 g of the desired E,E isomer which after crystallization from isopropyl ether melted at 117° C., and 0.8 g of the Z,E isomer.

Isomerization of the Z,E isomer into the E,E isomer

An iodine crystal was added at 20° C. to a solution of 0.8 g of Z,E isomer in 10 ml of toluene and the solution was refluxed for 18 hours and then evaporated to dryness to obtain a brown oil which was crystallized from isopropyl ether to obtain 0.53 g of crystals melting at 119° C. corresponding to the E,E isomer.

EXAMPLE 2

Methyl 2-(E) [[[2'-ethyl-(2,4'-bithiazol)-4-yl]-ethenyl]-2-phenyl]-3-methoxy-2-(E) propenoate 0.6 g of sodium hydride (50% in oil) were added at −5° and −10° C. to a solution of 6.6 g of the product of preparation 1, 2.25 g of [2'-ethyl-(2,4'-bithiazol)-4-yl]carbaldehyde [preparation 4 of the U.S. patent application No. 788,875] in 60 ml of tetrahydrofuran and 60 ml of dimethylformamide. The mixture was maintained for one hour at 0° C., then poured into water. After extraction with isopropyl ether, drying and concentrating, 4.2 g of crystals melting at 123° C. were obtained and were chromatographed on silica to obtain 1.98 g of the desired E,E isomer melting at 148° C. and 0.7 g of the Z,E isomer.

EXAMPLE 3

Methyl α (E) (methoxymethylene)-2-(E)-[[2-(2-pentyl)-4-thiazolyl]-ethenyl]-benzene-acetate Operating method 1

4,2 ml of diisopropylamine were added at −20° C. to a mixture of 6.5 g of lithium bromide in 45 ml of tetrahydrofuran, and the reaction medium was maintained for 10 minutes at −20° C. The solution was poured into a mixture at 0° C. of 16.5 g of the product of preparation 1, 300 ml of tetrahydrofuran and 5 g of 2-n-pentyl-4-thiazolyl-methanal [preparation 13 of the U.S. application No. 778,875]. The mixture was stirred for 2 hours at 0° C., then for 48 hours at ambient temperature and poured into water, followed by stirring and extraction with methylene chloride. The organic phases were dried and evaporated to dryness to obtain 20 g of crude product which was chromatographed on silica to obtain 5.03 g of the desired E,E isomer and 1.96 g of the Z,E isomer.

| NMR Constants | $\delta H_1$ | $\delta H_2$ | $JH_1H_2$ | $\delta H_3$ |
|---|---|---|---|---|
| E,E | | | 16 | 7.63 |
| Z,E | 6.54 | 6.65 | 12 | 7.49 |

Operating method 2

0.48 g of sodium hydride (50% in oil) were added between −5° and −10° C. to a solution of 5.7 g of phosphonium bromide (preparation 1), 1.8 g of 2-pentyl-4-thiazolyl-methanal in 50 ml of tetrahydrofuran and 50 ml of dimethylformamide and the reaction medium was maintained for one hour at 0° C. Using the above procedure, there was obtained 1.65 g of desired E,E isomer and 1.32 g of the Z,E isomer.

Isomerization of the Z,E isomer into the E,E isomer

An iodine crystal in 20 ml of toluene was added to a solution 1.9 g of Z,E isomer obtained as above and the solution was refluxed for 20 hours then cooled down and evaporated to dryness. After chromatography on silica, 1.8 g of the expected E,E isomer were obtained.

Preparation 1: [[2-[1-(methoxycarbonyl)-2-methoxy ethenyl]-phenyl]-methyl]-triphenyl phosphonium bromide STAGE A: methyl α 2-methyl phenyl acetate A mixture of 136 g of α 2-methyl-phenyl-acetic acid, 1400 ml of methanol and 1.4 ml of concentrated sulfuric acid was refluxed for one hour and then evaporated to dryness under reduced pressure. The residue was taken up in methylene chloride, washed with water and the organic phase was dried. After bringing to dryness under reduced pressure, 144 g of the desired product were obtained.

STAGE B: methyl 2-(2-methyl phenyl)-3-hydroxy-2-propenoate 2.9 g of sodium hydride (50% in oil) were introduced into 60 ml of tetrahydrofuran and 37 ml of methyl formate were introduced at 20°-25° C. The reaction mixture was stirred for 4 hours at 20°-25° C. and poured into 300 ml of 2N hydrochloric acid. Extraction was carried out with methylene chloride and the organic phase was dried and evaporated to dryness to obtain 8.2 g of product which was chromatographed on silica eluting with a hexane - ethyl acetate mixture (7-3). After bringing to dryness, 5.23 g of the desired product were obtained.

STAGE C: methyl Z-2-(2-methyl phenyl)-3-methoxy-2-propenoate and the corresponding E isomer A solution of 44 g of the product of Step B in 400 ml of tetrahydrofuran was introduced at 20°-25° C. into a solution of 700 ml of tetrahydrofuran and 11 g of sodium hydride (50% in oil). The reaction mixture was stirred for one hour and 150 ml of methyl iodide were added. The mixture was stirred for 5 hours and poured into water. Extraction was carried out with methylene chloride and the extracts were dried and brought to dryness to obtain 47.2 g of product which was chromatographed on silica and eluted with hexane-ethyl acetate mixture (7-3) to obtain the following:

a) a fraction with a Rf=0.3 which was evaporated to dryness under reduced pressure to obtain 1.9 g of the desired E isomer product.

| NMR CDCl$_3$, TMS | |
|---|---|
| H of the methylphenyl methyl | 2.18 ppm |
| H of the phenyl | 7.07 to 7.22 ppm |
| Ethylene H | 7.55 ppm |
| H of the OCH$_3$'s | 3.68 and 3.79 ppm | b) a fraction with a Rf=0.25 which was evaporated to dryness under reduced pressure to obtain 36 g of the desired Z isomer product.

| NMR CDCl$_3$, TMS | |
|---|---|
| H of the methylphenyl methyl | 2.22 ppm |
| H of the phenyl | 7.10 to 7.23 ppm |
| Ethylene H | 6.53 ppm |
| H of the OCH$_3$'s | 3.70 and 3.91 ppm |

STAGE D: Methyl E-(2-bromo-methylphenyl)-3-methoxy-2-propenoate

A mixture of 36 g of the product of Stage C (Δ Z), 500 ml of carbon tetrachloride, 32.6 g of N-bromosuccinimide and 200 mg of azodiisobutyronitrile was refluxed for 4 hours, then cooled down to 20° C., separated and evaporated to dryness under reduced pressure.

The 59 g of product obtained was chromatographed on silica eluting with a hexane - ethyl acetate mixture (7-3) to obtain 48.5 g of the desired product (Δ E).

| NMR CDCl$_3$, TMS | |
|---|---|
| H of CH$_2$Bz | 4.40 ppm |
| H of the phenyl | 7.1 to 7.5 ppm |
| Ethylene H | 7.63 |

| NMR CDCl$_3$, TMS | |
|---|---|
| H of the OCH$_3$'s | 3.69 and 3.80 |

STAGE E: [[2-[1-(methoxycarbonyl)-2-methoxy-ethenyl]-phenyl]-methyl]-triphenyl phosphonium bromide A mixture of 64 g of the product of Stage D, 650 ml of toluene and 59 g of triphenylphosphine was refluxed for 2 hours 30 minutes and the reaction mixture was allowed to return to ambient temperature, then separated, washed with toluene and with isopropyl ether and dried to obtain 88 g of the desired product.

| IR Spectrum | |
|---|---|
| > = O | 1700 cm$^{-1}$ |
| C = C | 1628 cm$^{-1}$ |
| Aromatic | 1600, 1588, 1492, 1482 cm$^{-1}$ |

| NMR - 250 MHz, CDCl$_3$, TMS | |
|---|---|
| H of the CH$_3$'s | 3.44 and 3.90 ppm |
| H of the —$\underline{CH_2}$P$^+$ | 4.85 ppm |
| H of the phenyls | 6.85 to 7.8 ppm |
| Ethylene H | 7.49 ppm |

FUNGICIDAL BIOLOGICAL ACTIVITY a) *Botrytis cinerea* trials on vines

Young vine plants grown from cuttings (N Grenache variety, clone 70) were cultivated in a greenhouse (day temperature: 30° C. night temperature: 25° C.) in a mixture of earth/compost/sand (⅓-⅓-⅓). Two days before the trial, the plants were taken to a cultivation chamber (same temperature conditions, humidity: 60% daytime, 80% nightime) and the product was dissolved in "matrix A" at a concentration of 500 ppm just before use. The treatment was achieved by spraying the solution on the leaves until maximum retention. The Botrytis spores were suspended in diluted carrot juice at the rate of 50,000 spores per ml. The contamination was effected by depositing the spore suspension in the form of drops (20 microliters) on the abaxial surface of the leaves. In the preventive trial, the treatment was effected the day before contamination. The plants were then kept in the cultivation chamber under the same conditions as previously. The readings were taken nine days after contamination by measuring the necrotic surfaces. The efficiency of the product was calculated with reference to a non-treated control.

b) *Plasmopara viticola* trials

The vegetal material used was the same as that used in trial A and grown under the same conditions. The treatment was also effected in the same way. The contamination was done with zoosporangium *Plasmopara viticola* taken immediately before the trial (50,000 zoozporangium per ml). The drops of the suspension (20 microliters) were deposited on the abaxial face of the leaves. The plants were then maintained for 24 hours in an atmosphere of saturated humidity, then taken into the humidity of the cultivation chamber (60% daytime, 80% nightime). The readings were taken ten days after contamination by measuring the development of pockets of conidiophores on the abaxial surface of the leaves. The efficiency of the product was calculated with reference to a non-treated control.

c) *Erysiphe graminis hordei* trials

The barley seeds (Pression variety) were put to germinate in the earth/compost/sand mixture (⅓,⅓,⅓) and grown in a greenhouse. The products were dissolved in "matrix A" just before the trial at a concentration of 500 ppm. The treatment was effected by spraying the product solution on ten day old barley plants until maximum retention was achieved. Contamination by the conidia of *Erysiphe graminis hordei* was done three days after treatment. The plants were kept in an air-conditioned room (day temperature: 23° C., night temperature: 18° C. and seven days after contamination, the extent of conidian felt-like cover on the first and second leaf of each plant was measured. The efficiency of the product was calculated with reference to a non-treated control.

d) *Gaeumannomyces graminis tritici* trials

Preparation of the inoculum: 200 g of autoclaved oat seeds were contaminated with *Gaeumannomyces graminis tritici*, and preserved for seven weeks at a temperature of 22° C. away from the light. The inoculum was then dried, reduced to a powder and preserved in this form. On the day of the trial, the washed and damped vermiculite was contaminated with the inoculum (1% by weight of inoculum) and distributed among the cultivation pots (100 g per pot). A 2 cm non-contaminated layer of vermiculite was deposited on the surface of the pots. Wheat grains (Cappelle variety) were spread in this upper layer. The products were dissolved in "Matrix A" at a concentration of 50 ppm and the treatment was effected by sprinkling each pot with 30 ml of the solution of the product. The pots were kept in a cultivation chamber (day temperature: 21° C., night temperature: 16° C.) and the weight of the parts above ground and of the root parts of each plant was measured three weeks after the sowing. The efficiency of the treatment was calculated with reference to a non-contaminated control and a non-treated contamined control.

e) *Puccinia recondita tritici* trials

Corn grains (Festival variety) were put to germinate in an earth/compost/sand mixture ⅓-⅓-⅓. The plants are cultivated in a greenhouse. The products are dissolved in the matrix A just before the trial at a concentration of 500 ppm. The treatment is effected by spraying the product solution on the nine day old corn plants, until maximum retention is achieved. Contamination by *Puccinia recondita tritici* uredospores is effected the day after the treatment. The plants are kept in an air conditioned room (day temperature: 22° C., night temperature: 18° C.). Seven days after the contamination the density of the spores on the first and second leaf of each plant is measured.

The efficiency of the product is calculated with reference to a non-treated control.

| | | Biological properties Fungicide properties. | | | | | |
|---|---|---|---|---|---|---|---|
| | Botrytis | Palsmo-para | Erysiphe 1st | 2nd | Gacumano | | Puccinia |
| Ex. | (pre) | (pre) | leaf | leaf | leaf | root | |
| 1 | | | 60 | | | | 80 |
| 5 | — | 10 | 30 | 50 | 10 | 100 | 40 |
| 14 | — | 40 | 90 | 70 | 0 | 0 | |
| 15 | 30 | 20 | 70 | 50 | 0 | 0 | 70 |
| 11 (E) | 80 | 70 | — | — | 0 | 10 | 30 |
| 11 (Z) | 20 | 100 | 50 | 30 | 0 | 0 | 30 |
| 17 | 70 | 70 | 60 | 40 | 0 | 0 | — |
| 16 | 80 | 100 | 70 | 50 | — | — | 50 |
| 20 | 40 | | 100 | 50 | — | — | 10 |
| 28 | 80 | | 100 | 40 | — | — | 30 |
| 29 | 100 | | 60 | 60 | — | — | 100 |
| 30 | 70 | — | — | 40 | — | — | 90 |
| 31 | 90 | — | — | — | — | — | 100 |
| 32 | 100 | — | 60 | 60 | — | — | 100 |
| 33 | 100 | — | 50 | 60 | — | — | 100 |
| 38 | 70 | — | 30 | 30 | — | — | 70 |

Various modifications of the process of the invention may be made without departing from the spirit or scope thereof and it is to be understood that the invention is intended to be limited only as defined in the appended claims.

What is claimed is:

1. A process for the preparation of a compound of the formula

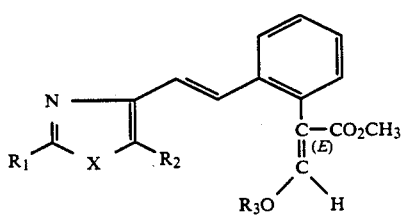

I wherein $R_1$ and $R_2$ are individually selected from the group consisting of hydrogen, halogen, —$CF_3$, alkyl, alkoxy and alkylthio of 1 to 8 carbon atoms, alkenyl and alkynyl of 2 to 8 carbon atoms, —$SO_2$alk and alk is alkyl of 1 to 8 carbon atoms, optionally substituted aryl, aryloxy and arylthio of 6 to 18 carbon atoms and optionally substituted heteroaryl and heteroaryloxy wherein the heteroaryl is selected from the group consisting of furyl, pyridinyl, benzofuranyl, isobenzofuranyl, oxazolyl, isoxazolyl, and thiazolyl and heterocyclic selected from the group consisting of piperazinyl morpholinyl, pyranyl and pyridazinyl, $R_3$ is selected from the group consisting of alkyl of 1 to 8 carbon atoms, alkenyl and alkynyl of 2 to 8 carbon atoms, aryl of 6 to 18 carbon atoms and alkoxyalkoxyalkyl of 3 to 14 carbon atoms, X is selected from the group consisting of —O—, —S— and —$NR_4$—, $R_4$ is selected from the group consisting of hydrogen, alkyl, alkenyl and alkynyl of up to 8 carbon atoms, —$SO_2$ alkyl, —$SO_2$ alkenyl and —$SO_2$ alkynyl of up to 8 carbon atoms and optionally substituted aryl and —$SO_2$ aryl of 6 to 18 carbon atoms, the optional substituents being selected from the group consisting of free, esterified or etherified hydroxyl in which the ester or ether part has 1 to 18 carbon atoms, ketone and oxime functions, saturated or unsaturated, linear, branched or cyclized alkyls of up to 18 carbon atoms, halogen, —$CF_3$, —$SCF_3$, —$OCF_3$, —$NO_2$, —$NH_2$ and —C≡N the double bond between the heterocycle of 5 member ring and the aromatic nucleus is of E and/or Z geometry comprising reacting a halide of the formula

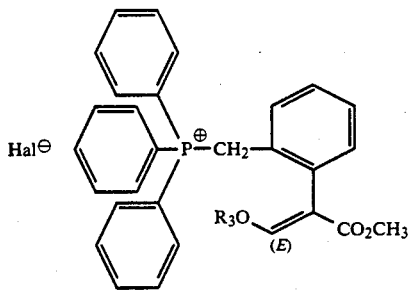

wherein $R_3$ is as defined above and Hal is halogen with a compound of the formula

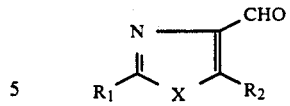

wherein X, $R_1$ and $R_2$ have the above definitions in the presence of a base selected from the group consisting of sodium hydride, alkali metal or alkaline earth metal alcoholate, an alkali metal amide or a secondary or tertiary amine in the presence of lithium bromide to obtain the corresponding product of formula I in the form of a mixture of isomers and optionally separating the isomers.

2. The process of claim 1 wherein $R_3$ is methyl.

3. The process of claim 1 wherein Hal is bromine.

4. The process of claim 1 wherein the base is a secondary or tertiary amine in the presence of lithium bromide.

5. The process of claim 1 wherein the base is sodium hydride.

6. The process of claim 1 wherein the Z,E isomer configuration is isomerized to E,E isomer by the action of iodine.

* * * * *